US006143313A

United States Patent [19]

Ito et al.

[11] Patent Number: 6,143,313

[45] Date of Patent: *Nov. 7, 2000

[54] INSECT PEST CONTROL METHOD

[75] Inventors: Tatsuei Ito, Hyogo; Mitsuyoshi Suzue, Tokushima; Masanaga Yamaguchi, Hyogo, all of Japan

[73] Assignee: Earth Chemical Co., Ltd., Tokyo, Japan

[ * ] Notice: This patent issued on a continued prosecution application filed under 37 CFR 1.53(d), and is subject to the twenty year patent term provisions of 35 U.S.C. 154(a)(2).

[21] Appl. No.: 08/776,887

[22] PCT Filed: Aug. 7, 1995

[86] PCT No.: PCT/JP95/01568

§ 371 Date: Feb. 10, 1997

§ 102(e) Date: Feb. 10, 1997

[87] PCT Pub. No.: WO96/04786

PCT Pub. Date: Feb. 22, 1996

[30] Foreign Application Priority Data

Aug. 8, 1994 [JP] Japan .................................... 6-185986

[51] Int. Cl.$^7$ ............................ A01N 25/10; A01N 53/00

[52] U.S. Cl. .......................... 424/409; 424/405; 514/461; 514/531

[58] Field of Search ...................... 43/113, 131; 424/405, 424/409, 421, DIG. 10; 514/919, 461, 531

[56] References Cited

U.S. PATENT DOCUMENTS

| | | | |
|---|---|---|---|
| 3,336,694 | 8/1967 | O'Connell | 43/139 |
| 4,282,673 | 8/1981 | Focks et al. | 43/113 |
| 4,310,985 | 1/1982 | Foster et al. | 43/131 |
| 5,091,423 | 2/1992 | Wilson et al. | 514/690 |

FOREIGN PATENT DOCUMENTS

| | | |
|---|---|---|
| 2282309 | 11/1990 | Japan . |
| 6165631 | 6/1994 | Japan . |

OTHER PUBLICATIONS

Mount et al : Mosquitoe News (1975), 35(1), 63–6 Toxicity of Pyrethroid & Organophosphorus Adulticides to 5 Species of Mosquitoes.

*Primary Examiner*—Neil S. Levy
*Attorney, Agent, or Firm*—Sughrue, Mion, Zinn, Macpeak & Seas, PLLC

[57] ABSTRACT

Provided is a technique comprising blowing air onto a carrier having supported thereon a preparation containing a highly safe pesticidal component to vaporize and diffuse the component from the preparation under non-heating conditions thereby to control flying insect pests. An insect pest control method characterized by preparing a preparation-retaining material by supporting on a carrier a preparation containing a pesticidal component which is hard to vaporize at normal temperature, preferably at least one pesticidal component selected from compounds which are hard to vaporize at normal temperature and have a vapor pressure of lower than $1\times10^{-3}$ mmHg and a boiling point of not lower than 120° C./1 mmHg, setting the resulting preparation-retaining material, and contacting the preparation with an air current raised by an air blowing means to release the component into the air under non-heating conditions, an apparatus suitable therefor, and a carrier to be used in the preparation-retaining material set in the apparatus characterized by not blocking the air current toward the vent hole of the apparatus are provided.

5 Claims, 11 Drawing Sheets

INSECT PEST CONTROL METHOD

TECHNICAL FIELD

The present invention relates to an insect pest control method. More particularly, it relates to an insect pest control method, especially flying insects, using a preparation-retaining material comprising a carrier having supported thereon a preparation containing a pesticidal component which is hard to vaporize at normal temperature, in which the pesticidal component is released from the preparation-retaining material by making use of an air current raised by a blower means under non-heating conditions; an apparatus suitable therefor; and a carrier constituting the preparation-retaining material.

BACKGROUND ART

A great number of pesticidal preparations have been proposed, and a proper preparation is selected therefrom for practical use in accordance with the insect to be controlled. In particular, preparations containing a vaporizing pesticidal component, i.e., those having a high vapor pressure at normal temperature have been used for flying insects such as mosquitos. The problem in using vaporizing components is that the preparations tends to vaporize and lessen its effect before use, for example, during storage. In order to prevent a preparation from vaporizing during storage and to let the preparation be released in a necessary concentration upon use, insect pest control has been carried out frequently by vaporizing a preparation under heating conditions. The pesticidal components contained in this type of preparations which are used under heating conditions usually have a vapor pressure of $1\times10^{-3}$ mmHg or lower at 30° C.

As an example of insect pest control by vaporizing a preparation under heating conditions, it is cited that a mosquito coil is a spiral coil molded from a kneaded mixture of a preparation and a slow-burning support, which is lit up and burnt whereby the preparation is vaporized by the heat. Pesticidal components useful for mosquito coils include pyrethrin, allethrin, and empenthrin. A mat type or liquid type electric mosquito control apparatus comprises an appropriate support impregnated with a preparation containing a pesticidal component, a part of the impregnated support of which is heated with a heater and the like to release the preparation. Pesticidal components useful for these types include allethrin, furamethrin, and prallethrin. Pesticidal components used in preparations for fumigation or evaporation which release a preparation in a short time period by heating with a heat source, such as heat of combustion or chemical reaction, include methoxadiazone, permethrin, and dichlorvos (Kateiyo Sacchuzai Gairon, Japan Sacchuzai Kogyokai (1991)).

Methods for forcibly vaporizing a preparation by ventilation are known. To cite an example, JU-A-55-954 (unexamined published Japanese utility model application) discloses a pesticidal apparatus having put therein a sublimating insect repellent, such as naphthalene, which inhales outer air through a hole to make the vaporizing component of the repellent vaporize and discharges air containing the vapor through a venting hole. Furthermore, a method for killing insects in which a diffusing material retaining a normal temperature vaporizing preparation, which is shaped into, e.g., a fan, is driven by a driving means to diffuse the vaporizing preparation is also known. This method, although regarded as one method for vaporizing a preparation under non-heating conditions, is considered to be effective when applied to preparations having relatively high vaporizability.

In the above-cited example of the method for vaporizing a preparation by ventilation, it is described that the air to be blown should be hot air when a pesticidal preparation whose vapor pressure ranges from $1\times10^{-3}$ mmHg to $1\times10^{-6}$ mmHg at 30° C. is used.

Spraying with aerosol is the only known means for diffusing a pesticidal component having a vapor pressure of $1\times10^{-3}$ mmHg to $1\times10^{-6}$ mmHg at 30° C. in space under non-heating conditions for insect control.

For control of flying insect pests, insecticides having high insecticidal activity and a very high vapor pressure, such as DDVP having a vapor pressure of $1\times10^{-2}$ mmHg at 30° C., have been put to practical use in the form of a vaporizing preparation comprising a resin matrix because of simplicity of use and also because there is no danger of increasing the surrounding temperature or causing burns.

However, DDPV is an organophosphorus compound, the safety of which is a concern. Therefore, vaporizing preparations of other chemicals have been sought for. When an insecticide other than organophosphorus compounds, for example, empenthrin is formulated into a vaporizing preparation, the preparation is effective only in a confined system. It has been used in practice only in deserted places, such as a septic tank, and places closed for a long time, such as a wardrobe and a chest of drawers.

As stated above, most of the insecticidal preparations used against insect pests, especially flying insects, are usually of the type that the active ingredient thereof is vaporized and diffused under heating conditions. This type of preparations require much energy and entertain a danger of increasing the temperature of the equipment or the surrounding temperature and a burn.

Where an active ingredient of an insecticidal preparation is to be vaporized at normal temperature without any heating means, the active ingredient to be used must have a high vapor pressure at normal temperature so as to be supplied to the space in a sufficient concentration. DDVP and the like which have a high vapor pressure at normal temperature have a safety problem. Thus, there has been no effective means available as yet in which a preparation used is safe and hard to vaporize at normal temperature, that is, does not decrease before use but, in use, can be supplied to the surrounding space in a sufficient concentration under non-heating conditions.

Hence it has been keenly demanded to develop a means for controlling insect pests which eliminates the above-mentioned problems by vaporizing and diffusing a highly safe active ingredient under non-heating conditions.

DISCLOSURE OF THE INVENTION

The inventors of the present invention have extensively studied on control of insect pests by releasing under non-heating conditions a pesticidal preparation that has usually been used by vaporizing and diffusing the active ingredient under heating conditions, and completed the invention.

The present invention is characterized by the following: ps (1) An insect pest control method which comprises: supporting on a carrier a preparation containing at least one pesticidal component selected from compounds which are hard to vaporize at normal temperature to prepare a preparation-retaining material; setting the preparation-retaining material to contact the preparation with an air current raised by a blower means; and releasing the pesticidal component from the preparation-retaining material into the air under non-heating conditions to control insect pests.

(2) An insect pest control method which comprises: supporting on a carrier a preparation containing at least one pesticidal component selected from compounds which are hard to vaporize at normal temperature to prepare a preparation-retaining material, said compounds being 1-ethynyl-2-methyl-2-pentenyl dl-cis/trans-3-(2,2-dimethylvinyl)-2,2-dimethyl-1-cyclopropanecarboxylate, d-trans-2,3,5,6-tetrafluorobenzyl-3-(2,2-dichlorovinyl)-2,2-dimethyl-1-cyclopropanecarboxylate, (5-benzyl-3-furyl) methyl d-cis/trans-chrysanthemate, d-3-allyl-2-methyl-4-oxo-2-cyclopentenyl d-trans-chrysanthemate, 5-propargyl-2-furylmethyl d-cis/trans-chrysanthemate, (+)-2-methyl-4-oxo-3-(2-propynyl)-2-cyclopentenyl (+)-cis/trans-chrysanthemate, dl-3-allyl-2-methyl-4-oxo-2-cyclopentenyl dl-cis/trans-2,2,3,3-tetramethylcyclopropanecarboxylate and/or isomers thereof and/or analogues thereof; setting the preparation-retaining material to contact the preparation with an air current raised by a blower means; and releasing the pesticidal component from the preparation-retaining material into the air under non-heating conditions to control insect pests.

(3) An insect pest control apparatus which comprises a main body having a ventilation means led to a vent hole and a preparation-retaining material comprising a preparation supported on a carrier set at one or more locations within the ventilation means, wherein the preparation-retaining material contains at least one pesticidal component selected from compounds which are hard to vaporize at normal temperature; and the preparation-retaining material set in the ventilation means is brought into contact with an air current raised at the vent hole under non-heating conditions.

(4) An insect pest control apparatus which comprises a main body having a ventilation means led to a vent hole and a preparation-retaining material comiprising a preparation supported on a carrier set at one or more locations within the ventilation means, wherein the preparation-retaining material contains at least one pesticidal component selected from compounds which are hard to vaporize at normal temperature, said compounds being 1-ethynyl-2-methyl-2-pentenyl dl-cis/trans-3-(2,2-dimethylvinyl)-2,2-dimethyl-1-cyclopropanecarboxylate, d-trans-2,3,5,6-tetrafluorobenzyl-3-(2,2-dichlorovinyl)-2,2-dimethyl-1-cyclopropanecarboxylate, (5-benzyl-3-furyl)methyl d-cis/trans-chrysanthemate, d-3-allyl-2-methyl-4-oxo-2-cyclopentenyl d-trans-chrysanthemate, 5-propargyl-2-furylmethyl d-cis/trans-chrysanthemate, (+)-2-methyl-4-oxo-3-(2-propynyl)-2-cyclopentenyl (+)-cis/trans-chrysanthemate, dl-3-allyl-2-methyl-4-oxo-2-cyclopentenyl dl-cis/trans-2,2,3,3-tetramethylcyclopropanecarboxylate and/or isomers thereof and/or analogues thereof; and the preparation-retaining material is brought into contact with an air current raised at the vent hole under non-heating conditions.

(5) An insect pest control preparation used in the insect pest control method described in the above (1) or (2) or the insect pest control apparatus described in the above (3) or (4), which comprises at least one pesticidal component selected from compounds which are hard to vaporize at normal temperature, said compounds being 1-ethynyl-2-methyl-2-pentenyl dl-cis/trans-3-(2,2-dimethylvinyl)-2,2-dimethyl-1-cyclopropanecarboxylate, d-trans-2,3,5,6-tetrafluorobenzyl-3-(2,2-dichlorovinyl)-2,2-dimethyl-1-cyclopropanecarboxylate, (5-benzyl-3-furyl)methyl d-cis/trans-chrysanthemate, d-3-allyl-2-methyl-4-oxo-2-cyclopentenyl d-trans-chrysanthemate, 5-propargyl-2-furylmethyl d-cis/trans-chrysanthemate, (+)-2-methyl-4-oxo-3-(2-propynyl)-2-cyclopentenyl (+)-cis/trans-chrysanthemate, dl-3-allyl-2-methyl-4-oxo-2-cyclopentenyl dl-cis/trans-2,2,3,3-tetramethylcyclopropanecarboxylate and/or isomers thereof and/or analogues thereof.

(6) A carrier constituting a preparation-retaining material, wherein, when the preparation-retaining material comprising a preparation supported on a carrier is set within the ventilation means of the insect pest control apparatus described in the above (3), said preparation comprising at least one pesticidal component selected from compounds which are hard to vaporize at normal temperature and/or isomers thereof and/or analogues thereof, the material does not block an air current in the ventilation means.

(7) A carrier constituting a preparation-retaining material, wherein, when a preparation-retaining material comprising a preparation supported on a carrier is set within the ventilation means of the insect pest control apparatus described in the above (3), said preparation comprising at least one pesticidal component selected from the compounds described in the above (2), the material does not block an air current in the ventilation means.

As previously described, a method for vaporizing an pesticidal component from a preparation containing the same by blowing air thereby to control flying insects is known. However, preparations applicable to this method have been limited to those having a very high vapor pressure such as DDVP, or the method has been limited to use in a confined space. It has been believed impossible for a pesticidal component which is hard to vaporize at normal temperature and has a vapor pressure of not higher than $1\times10^{-3}$ mmHg at 30° C. to be released from a preparation containing the same in a concentration sufficient for insect pest control only by blowing air under non-heating conditions. Therefore, it has been far from anticipation that use of a preparation containing a pesticidal component which is hard to vaporize at normal temperature might produce an insecticidal effect in wide spaces such as a living room.

This seems to be partly because the right vapor pressures of many known pesticidal components at various temperatures have not determined, still less compared accurately.

The inventors of the present invention analyzed the vapor pressure at 30° C. of many compounds acting as a pesticidal component by using a cox diagram hereinafter described. In their study, a preparation-retaining material was prepared by supporting, on an appropriate carrier, a preparation containing a pesticidal component which was selected by taking the vapor pressure as a measure, and air was blown to the resulting preparation-retaining material set in a place to release the pesticidal component therefrom. As a result, the inventors unexpectedly found the method of the present invention. That is, when the preparation-retaining material is set, and air is applied thereto under non-heating conditions, the pesticidal component which is hard to vaporize is released therefrom, whereby insect pests such as flying insects can be controlled by the thus released component.

Embodiments of supporting a preparation containing a pesticidal component (inclusive of a component which inhibits a biting action of biting insects) on a carrier include, as hereinafter described in detail, not only a method in which the preparation is applied to a carrier, such as paper, porous resins, ceramics and the like, the resulting preparation-retaining material is put in a case, and air is applied to the preparation-retaining material as put in the case and set, but also a method in which a liquid preparation containing the pesticidal component is put in a bottle having the above-described carrier, such as paper and porous resins, in the form of, e.g., a sheet, which is pulled up out of the opening of the bottle so that the liquid may be sucked up, and air is applied to the carrier outside the bottle.

The conventional method in which a normal temperature vaporizing pesticidal component is vaporized without heating and letting out the vapor of the component from a vent hole is disadvantageous in that the vapor concentration is difficult to control. The conventional method in which a fan-shaped diffusing material retaining a vaporizing preparation is driven by a driving means to diffuse the vaporizing preparation is disadvantageous in that a burden is imposed on the driving means to damage it. Besides, the method of driving a diffusing material retaining a vaporizing preparation by a driving means is applicable only to normal temperature vaporizing preparations or effective only when used with warm air blowing conditions.

The method of the present invention comprises supporting a preparation containing a pesticidal component which is hard to vaporize at normal temperature on a carrier, contacting the preparation-retaining material in a fixed state with an air current by a blower means to release the pesticidal component, and controlling flying insects with the thus released preparation. Accordingly, the method of the present invention has such characteristics that the concentration of the vaporized component can be controlled easily and, since no heating means is used, there is no danger, and the apparatus therefor can be simple. The method is therefore an excellent means for releasing a pesticidal component.

The means for feeding air to the preparation-retaining material containing a pesticidal component may be a simple one, such as a fan that can be driven by a cell, as well as a blower means suitable for stable release of the preparation in a constant concentration over a long time period, e.g., for 30 days from the start of blowing. The details of the blower means will be described later.

The insect pest control is intended to inclusively mean extermination of insect pests, repelling insect pests, and inhibition of a blood sucking action or a biting action in blood-sucking insects. Emphasis should be placed here on the following points. (1) It has been found that the pesticidal components for use in the present invention show straight lines parallel to each other in their vapor pressure vs. temperature plots in a cox diagram. (2) Based on this result of study, it has now been made possible to evaluate the pesticidal effect of various compounds, inclusive of those which have only one known vapor pressure in a temperature range of from 20° C. to 50° C., when applied to the "method of releasing a pesticidal component only by blowing under non-heating conditions", by taking "the vapor pressure at a given temperature (30° C.)" as a common standard of evaluation. As a result, a new finding was obtained, based on which a new technique has been established.

An example of the cox diagram prepared on various pesticidal preparations is shown in FIG. 11.

In FIG. 11, a: DDVP; b: nitrapyrin; c: empenthrin; d: demeton-D; e: terallethrin (M 108); f: furamethrin; g: aldrin; h: prallethrin; i: allethrin; j: phosphamidon; k: methoprene; l: fluchloralin; m: resmethrin; n: tetramethrin; o: phenothrin; p: cyphenothrin; q: permethrin; r: S-fenvalerate; s: phthalthrin; and t: flucythrinate.

The vapor pressures of pyrethroid compounds measured at every 50° C. between 20° C. and 40° C. are shown in Table 1 below. The measurement was made with the vapor pressure measuring apparatus shown in FIG. 12 (the detailed explanation of the apparatus are omitted here) which is described in *Kagaku Kogyo Jikkenho* (4th ed.), Baifukan (1986). In Table 1, the underlined data are those from the literatures.

TABLE 1

Vapor Pressures of Pyrethroid Compounds

| Compound | Vapor Pressure (mmHg) 20° C. | 25° C. | 30° C. | 35° C. | 40° C. |
|---|---|---|---|---|---|
| prallethrin | $3.5 \times 10^{-5}$ | $6.9 \times 10^{-5}$ | $1.3 \times 10^{-4}$ | $2.4 \times 10^{-4}$ | $4.4 \times 10^{-4}$ |
| allethrin | $3.4 \times 10^{-5}$ | $6.3 \times 10^{-5}$ | $1.2 \times 10^{-4}$ | $2.2 \times 10^{-4}$ | $4.0 \times 10^{-4}$ |
| phthalthrin | $3.5 \times 10^{-8}$ | $6.6 \times 10^{-8}$ | $1.2 \times 10^{-7}$ | $2.2 \times 10^{-7}$ | $3.8 \times 10^{-7}$ |
| resmethrin | $3.5 \times 10^{-6}$ | $7.1 \times 10^{-6}$ | $1.7 \times 10^{-5}$ | $2.8 \times 10^{-5}$ | $5.6 \times 10^{-5}$ |
| phenothrin | $1.2 \times 10^{-6}$ | $2.2 \times 10^{-6}$ | $4.3 \times 10^{-6}$ | $7.7 \times 10^{-6}$ | $1.4 \times 10^{-5}$ |
| permethrin | $5.5 \times 10^{-7}$ | $1.1 \times 10^{-6}$ | $1.9 \times 10^{-6}$ | $3.6 \times 10^{-6}$ | $6.3 \times 10^{-6}$ |
| cyphenothrin | $9.2 \times 10^{-7}$ | $1.9 \times 10^{-6}$ | $3.6 \times 10^{-6}$ | $6.6 \times 10^{-6}$ | $1.3 \times 10^{-5}$ |
| empenthrin | $5.1 \times 10^{-4}$ | $9.2 \times 10^{-4}$ | $1.6 \times 10^{-3}$ | $2.8 \times 10^{-3}$ | $4.8 \times 10^{-3}$ |
| DDVP | $1.2 \times 10^{-2}$ | $1.9 \times 10^{-2}$ | $3.0 \times 10^{-2}$ | $4.6 \times 10^{-2}$ | $7.1 \times 10^{-2}$ |
| benfluthrin | $8.3 \times 10^{-5}$ | $1.5 \times 10^{-4}$ | $2.7 \times 10^{-4}$ | $4.0 \times 10^{-4}$ | $8.5 \times 10^{-4}$ |
| furamethrin | $1.3 \times 10^{-4}$ | $2.2 \times 10^{-4}$ | $4.5 \times 10^{-4}$ | $7.1 \times 10^{-4}$ | $1.4 \times 10^{-3}$ |
| tetramethrin | $2.4 \times 10^{-6}$ | $4.4 \times 10^{-6}$ | $8.5 \times 10^{-6}$ | $1.7 \times 10^{-5}$ | $3.2 \times 10^{-5}$ |
| terallethrin (M 108) | $2.2 \times 10^{-4}$ | $4.2 \times 10^{-4}$ | $6.6 \times 10^{-4}$ | $1.2 \times 10^{-3}$ | $4.8 \times 10^{-3}$ |

Note: The underlined data are from the literatures.

The vapor pressure data are available in the following literatures.

(i) *Noyakuno seizaigijutsu to kiso*, Nihon Shokubutsu Boeki Kyokai (1985)

(ii) *Noyaku Data Book*, Soft Science K.K. (1989)

(iii) Safety data (for terallethrin)

(iv) Product data (for furamethrin, tetramethrin and resmethrin)

Compounds which are hard to vaporize at normal temperature can be used in the present invention as a pesticidal component. Those having a vapor pressure higher than $1 \times 10^{-7}$ mmHg at 30° C. and a boiling point of not lower than 120° C./1 mmHg are preferred. It should be noted that the range of vapor pressure as referred to herein is the range at 30° C. on the vapor pressure vs. temperature plot in the cox diagram hereinafter described.

The vapor pressure of pesticidal components has conventionally been measured at an arbitrarily and randomly selected temperature, that is, under non-fixed measuring conditions. Usually, the measurement has been made at a temperature of from 10° C. to 50° C. It has therefore been difficult to compare a plurality of pesticidal preparations in terms of vapor pressure.

The results of our study have made it possible to suppose or know the vapor pressure at a target temperature by utilizing the cox diagram only if at least one found value is available. The aforesaid problem can thus be solved.

The cox diagram is illustrated below in detail.

When vapor pressure P is measured at varied temperature t for a large number of chemical substances, and log P [wherein P is a vapor pressure (mmHg)] is plotted as ordinate, and t/(t+C) [wherein t is a temperature (° C.); and C is a constant (usually 230)] as abscissa, it is known in engineering that the plot shows linearity with high precision.

In other words, a large number of chemical substances have the following relationship between temperature t and vapor pressure P at that temperature.

$$\log P = D + Et/(t+C)$$

Accordingly, the plot of logP as ordinate against t/(t+C) as abscissa gives a straight line.

The cox diagram as used herein is the straight line or a group of the straight lines obtained by plotting log P as ordinate and t/(t+C) as abscissa on a graph.

Among the pesticidal components whose vapor pressure has been measured within a temperature range of from 20° C. to 40° C., those having a vapor pressure of higher than $1\times10^{-7}$ mmHg at 30° C. in the above-mentioned cox diagram, being hard to vaporize at normal temperature, and having a boiling point of not lower than 120° C./1 mmHg are preferred. Furthermore, from the standpoint of safety, pyrethroid compounds are preferred. Typical examples of these preferred compounds are shown below:

dl-3-allyl-2-methyl-4-oxo-2-cyclopentenyl dl-cis/trans-chrysanthemate (common name: allethrin; trade name: Pynamin, produced by Sumitomo Chemical Co., Ltd.);

dl-3-allyl-2-methyl-4-oxo-2-cyclopentenyl d-cis/trans-chrysanthemate (trade name: Pynamin Forte, produced by Sumitomo Chemical Co., Ltd.; hereinafter referred to as "pynamin forte");

dl-3-allyl-2-methyl-4-oxo-2-cyclopentenyl d-trans-chrysanthemate (trade name: Bioallethrin, produced by Uclaf Co.);

d-3-allyl-2-methyl-4-oxo-2-cyclopentenyl d-trans-chrysanthemate (trade name: Exthrin, produced by Sumitomo Chemical Co., Ltd.; trade name: Esbiol, produced by Uclaf Co.; hereinafter referred to as "esbiol");

(5-benzyl-3-furyl)methyl d-cis/trans-chrysanthemate (common name: resmethrin; trade name: Chrysron Forte, produced by Sumitomo Chemical Co., Ltd.; hereinafter referred to as "resmethrin");

5-propargyl-2-furylmethyl d-cis/trans-chrysanthemate (common name: furamethrin; trade name: Pynamin D Forte, produced by Sumitomo Chemical Co., Ltd.; hereinafter referred to as "furamethrin");

(+)-2-methyl-4-oxo-3-(2-propynyl)-2-cyclopentenyl (+)-cis/trans-chrysanthemate (common name: prallethrin; trade name: Etoc, produced by Sumitomo Chemical Co., Ltd.; hereinafter referred to as "prallethrin");

dl-3-allyl-2-methyl-4-oxo-2-cyclopentenyl dl-cis/trans-2,2,3,3-tetramethylcyclopropanecarboxylate (common name: terallethrin; produced by Sumitomo Chemical Co., Ltd.; hereinafter referred to as terallethrin);

(1,3,4,5,6,7-hexahydro-1,3-dioxo-2-isoindolyl)methyl dl-cis/trans-chrysanthemate (common name: phthalthrin; trade name: Neopynamin, produced by Sumitomo Chemical Co., Ltd.);

(1,3,4,5,6,7-hexahydro-1,3-dioxo-2-isoindolyl)methyl d-cis/trans-chrysanthemate (trade name: Neopynamin Forte, produced by Sumitomo Chemical Co., Ltd.);

3-phenoxybenzyl-d-cis/trans-chrysanthemate (common name: phenothrin; trade name: Sumithrin, produced by Sumitomo Chemical Co., Ltd.);

3-phenoxybenzyl-dl-cis/trans-3-(2,2-dichlorovinyl)-2,2-dimethyl-1-cyclopropanecarboxylate (common name: permethrin; trade name: Eksmin, produced by Sumitomo Chemical Co., Ltd.);

(±) α-cyano-3-phenoxybenzyl (+)-cis/trans-chrysanthemate (common name: cyphenothrin; trade name: Gokilaht, produced by Sumitomo Chemical Co., Ltd.);

1-ethynyl-2-methyl-2-pentenyl dl-cis/trans-3-(2,2-dimethylvinyl)-2,2-dimethyl-1-cyclopropanecarboxylate (common name: empenthrin; trade name: Vaporthrin, produced by Sumitomo Chemical Co., Ltd.; hereinafter referred to as "empenthrin"); and d-trans-2,3,5,6-tetraf luorobenzyl-3-(2,2-dichlorovinyl)-2,2-dimethyl-1-cyclopropanecarboxylate (common name: benf luthrin).

In addition, compounds which are structurally similar (i.e., analogous) to the above-listed compounds can also be used. For empenthrin having two methyl groups at the 3-position, for instance, analogues having other alkyl groups, unsaturated alkyl groups or halogen atoms in place of the methyl groups can be used.

In the present invention, at least one pesticidal component selected from these compounds is used in the form of a preparation-retaining material.

Of the above-listed compounds particularly preferred are empenthrin, prallethrin, resmethrin, esbiol, furamethrin, and terallethrin. As long as the above-described conditions are satisfied, other pesticidal components, such as organophosphorus compounds, carbamate compounds, and insect growth inhibitory agents (IGR, JH and the like), can be used alone or in combination with no particular limitation. Analogues to these compounds are also useful.

The carrier which constitutes the preparation-retaining material of the present invention preferably has good ventilation so as not to block the air current from a blower means nor to diffuse the air current in unnecessary directions. It is desirable for the carrier to retain a sufficient amount of a preparation (pesticidal component and the like). Any material that has good ventilation and can retain a sufficient amount of a preparation can be used with no particular limitation.

Carriers having a honeycomb structure, a structure like a ventilation blind, a lattice structure, a network structure or the like are preferred for their structural simpleness and good ventilation.

The carrier to be used usually has such ventilation as has an air permeability of not less than 0.1 l/sec, preferably not less than 0.1 l/sec.

The carrier can be made of organic or inorganic molding materials. Molded articles obtained from these materials as a carrier include paper (e.g., filter paper, pulp, cardboard and the like), resins (e.g., polyethylene, polypropylene, polyvinyl chloride, oil-absorbing polymers and the like), ceramics, glass fiber, carbon fiber, chemical fiber (e.g., polyester, nylon, acrylic resins, vinylon, polyethylene, polypropylene and the like), natural fiber (e.g., cotton, silk, wool, hemp, and the like), and nonwoven fabric made of glass fiber, carbon fiber, chemical fiber, natural fiber and the like, porous glass materials, metallic nets and the like.

One of these carriers in which a preparation containing the pesticidal component is retained or a combination of two or more thereof is used in an arbitrary shape.

A carrier for adsorption (i.e., an auxiliary material for retaining a preparation on a carrier) can be used in combination. Such a carrier for adsorption includes gelling material (e.g., agar, caragenan, starch, gelatin, alginic acid and the like) and plasticized high polymers. High polymers can be plasticized with, for example, dioctyl phthalate.

The vaporizing properties of the preparation can be improved by addition of a sublimating substance, such as adamantane, cyclododecane, cyclodecane, norbornane, trimethylnorbornane, naphthalene, and camphor, as a vaporization accelerator. Also, the preparation may contain a synergist known for an active pyrethroid component, such as α-[2-(2-butoxyethoxy)ethoxy]-4,5-methylenedioxy-2-propyltoluene (piperonyl butoxide), N-(2-ethylhexyl) bicyclo[2,2,1]hept-5-ene-2,3-dicarboximide (MGK-264), octachlorodiisopropyl ether (S-421), synepirin 500 and the like.

In order to increase stability to light, heat, and oxidation and thereby to stabilize the effect, an antioxidant or an ultraviolet absorber can be added to the preparation. Useful antioxidants include 2'-methylenebis(6-t-butyl-4-ethylphenol) 2,6-di-t-butyl-4-methylphenol (BHT), 2,6-di-t-butylphenol, 2,2'-methylenebis(6-t-butyl-4-methylphenol), 4,4'-methylenebis(2,6-di-t-butylphenol), 4,4'-butylidenebis(6-t-butyl-3-methylphenol), 4,4'-thiobis (6-t-butyl-3-methylphenol), and dibutylhydroxinone (DBH). Useful ultraviolet absorbers include phenol derivatives (e.g., BHT), bisphenol derivatives, arylamines (e.g., phenyl-α-naphtylamine, a condensate between phenetidine and acetone), and benzophenone compounds.

In the embodiment in which the preparation is absorbed and retained in the preparation-retaining material and is vaporized by feeding air or the like, an indicator directly or indirectly indicative of the residual amount of the preparation can be used. For example, a function as an indicator can be added to the carrier by using a dye that causes the carrier to change its color, such as allylaminoanthraquinone, 1,4-diisopropylaminoanthraquinone, 1,4-diaminoanthraquinone, 1,4-dibutylaminoanthraquinone, 1-amino-4-anilinoanthraquinone, and the like. A function of indicating the residual amount of the preparation can also be added by using an electron-donating organic compound having a lactone ring or a color developer having a phenolic hydroxyl group, and, if desired, a desensitizer; these compounds cause the carrier to change its color with vaporization of the preparation (and the desensitizer vaporizing at the same time). Perfumes generally used in compositions for vaporization may be added to the preparation.

In the embodiment in which a liquid preparation is put in a bottle and sucked up by absorption in a carrier in the outside of the bottle, and air is blown to the carrier outside the bottle to vaporize the preparation, there is no need to use an indicator as far as the bottle allows confirmation of the residual amount of the liquid contained therein.

The preparation (containing the pesticidal component, and the like) can be retained in or on a carrier by applying a liquid preparation to the carrier by dropping, impregnation, spraying, printing, brush or the like coating, or by sticking a preparation onto the carrier. In using a non-liquid or solventless preparation, it can be applied to a carrier by kneading, coating, printing or the like. Also, the preparation may be applied either all over the carrier or partly, i.e., the preparation may be applied in spots or pattern or applied to only one side of the carrier.

In another embodiment of retaining the preparation in a carrier, the preparation is charged in a bottle for liquid and is migrated to a vaporizing zone through a porous carrier.

In order to facilitate application of a liquid preparation to the carrier by impregnation, an organic solvent, such as fatty acid esters (e.g., isopropyl myristate, isopropyl palmitate, hexyl laurate or the like), isopropyl alcohol, polyethylene glycol, deodorized kerosine, and the like, can be used if desired as an additive for reducing the viscosity.

The amount of the pesticidal component and/or other various components to be retained on/in the carrier is not particularly limited. Where an oil-absorbing material (e.g., paper) is used as a carrier, for instance, the preparation (containing the pesticidal component and the like) is infiltrated into the carrier in an amount of from 50 to 1000 mg, preferably of from 100 to 700 mg, per gram of the carrier. The above range corresponds to a range of from the minimum for assuring a minimum rate of vaporization of 0.1 mg/hr up to a point of saturation.

As shown in FIG. 2, the apparatus according to the present invention has an air passageway indicated by reference numeral 13 and vent holes (air intake 12 and vapor outlet 14). Where the preparation-retaining material is set in air passageway 13, it is fixed at at least one location in the air passageway (indicated by reference numeral 5 in FIG. 1 and reference numeral 30 in FIG. 2). The manner of fixing the preparation-retaining material (5 or 30) in airy passageway 13 is not particularly limited. For example, a groove, a guide, a stabilizing tool, or a holding element for fixing the carrier can be provided in the air passageway.

The ventilation means used here, specifically the air passageway, is a passageway or a space in which an air current raised at the vent holes runs. However, the passageway is not always necessary. The vent holes include an air intake for letting in outside air and a vapor outlet for letting out the air having been let in.

The air current is explained below by referring to FIGS. 1 and 2. The apparatus is fitted with a driving means, such as a motor, a spiral spring or the like, and equipment usually called a blower having such a shape, a form and a function as is commonly recognized as a fan, such as a propeller fan (indicated by reference numeral 6 in FIG. 1 and reference numeral 20 in FIG. 2). The fan is operated by the driving means to suck in outside air through the air intake. The air sucked in moves through the passageway toward the vapor outlet. Since revolution of the fan is accompanied by eddies, the air sucked in from the air intake is characterized in that the current rate becomes slower toward the center of the fan and faster toward the periphery of the fan. Accordingly, the amount of air applied to the carrier retaining the preparation is smaller in the vicinities of the center of the carrier and larger in the peripheral portions. It follows that the diffusion of the vapor of the preparation at various parts of the carrier is non-uniform. To cope with this problem, it is desirable to put a current regulator (for example, the member shown in FIG. 4 with reference numeral 40) in the air passageway. The current regulator is provided for leveling the current of air applied to the preparation-retaining material, but it should have such a shape as minimizes a pressure loss so as to minimize the power for revolution of the fan.

The air having been applied to the preparation-retaining material is discharged outside, whereby the active ingredient of the preparation is released from the preparation-retaining material set in the air passageway, made to current, let out through the vapor outlet, and diffused outside together with the air current.

For practical use, a small-sized blower suffices for such a space as a living room of common houses. Specifically, a fan is used at about 500 to 10000 rpm, and a motor or a spiral spring can be used as a driving means. A piezoelectric fan that does not rely on a motor or a spring can also be used. For use in a space like a living room, use of a fan that can be driven with a small motor powered by a solar battery, a secondary battery or a dry battery produces a sufficient effect. Where a dry battery is insufficient for a long-term use, a rechargeable battery may be used, or driving energy can be obtained continuously from a power source through a cord with a plug.

A centrifugal fan is generally used. The performance of a fan depends on not only its shape but the shape of a partition placed at the rear of the fan.

The shape of a fan is not limited to a screw or a propeller, and a waterwheel type fan, a rotary fan and the like can also be used. A screw fan, a propeller fan and the like are suitable for obtaining a large blowing action, having an advantage that the degree of vaporization can be increased by blowing. In order to increase the air brought into contact with a fan, each blade of the fan may have openings. For example, a large number of openings are made in the blades to efficiently vaporization and diffuse the preparation. The openings can have a variety of forms, such as a network shape, a lattice shape, a honeycomb shape and the like. The openings are preferably provided as uniformly as possible. The shape of the blades is decided according to the shape of the fan. Not only a mere plate but a hollow blade may be used.

Of various types of fans, what we call a sirocco fan 42 shown in FIG. 5 is preferably used. The fan 42 has adjustable blowing ability with variations of a power source including from batteries to adapters and of the voltage applied. The air current is also adjustable by altering the shape of the fan. For example, the air current can be increased by increasing the diameter or thickness, and vice versa.

The air intake is preferably located as near as possible to the front of the impeller but may be slightly shifted in relation to the position where a preparation-retaining material is to be set.

The vapor outlet is preferably provided in the circumferential direction for efficient diffusion of the vapor outside. The outlet is provided in at least one direction. When smoother diffusion is required, the vapor outlet is provided in two to four directions thereby to diffuse the vapor throughout the space. In a conventional system in which a carrier having supported thereon a vaporizing preparation is placed near the vapor outlet, where the vapor outlet is provided around the whole circumference of the apparatus, the carrier should be provided around the whole circumference of the apparatus. This is not necessary in the present invention, and yet the preparation can be diffused toward every direction. If desired, guides can be provided to control the air current so that the vapor of the preparation may not be diffused inside around the circumference, for example, may be discharged in only one direction.

Where such a fan as a sirocco fan is used, the preparation-retaining material is placed in the front of the fan unlike the embodiments shown in FIGS. 1 and 2. Therefore, it is desirable to use an air-permeable carrier so that the air current sucked in may not be cut or hindered and diffused outward.

Whether the preparation-retaining material is set in the air intake side or vapor outlet side of the fan appears to make no difference. However, when it is set in the intake side of the fan, the speed of air current applied to the preparation-retaining material is relatively uniform irrespective of the part thereof, whereas if it is set in the outlet side of the fan, the air current greatly varies in speed from part to part, while dependent on the shape of the fan. Accordingly, it is desirable in the latter case that the air current is made uniform by, for example, providing a current regulator in the air passageway as described previously.

The preparation-retaining material is preferably set in the air intake side because, if not, vaporization of the preparation tends to vary greatly with place. The position of the preparation-retaining material does not need to be right in front of the fan and may be shifted therefrom slightly, provided that the preparation-retaining material is in the air current sucked in through the intake toward the fan.

In more detail, the distance between the fan as a blowing means and the carrier supporting the preparation is preferably not so close to each other, and they are preferably spaced at about 5 mm or more. If they are so close to each other, it is difficult to apply air uniformly all over the carrier, tending to result in unevenness of vaporization, i.e., insufficient vaporization at the peripheral portion as compared with the central portion. For example, in the case where a paper-made honeycomb structure (70×70×15 mm) is used as a carrier, and air is blown with a sirocco fan (5 cm in diameter; 2 cm in thickness), when the power voltage for driving the fan is varied from 2.0 V to 4.0 V, a preferred distance between the carrier and the fan is 5 to 15 mm. The above range of the distance is not limitative, and the distance can be selected appropriately according to the shapes of the carrier and the fan, the power voltage, the shape and size of the apparatus, the relation among these factors, a combination of these factors, and the like.

The effectiveness of the fan type insect pest control apparatus of the present invention was tested as follows. As shown in FIG. 6, the apparatus was placed on the center of the floor of a room having a capacity of 36 $m^3$. After the release of the preparation was started, air in the room was sucked up at a constant amount of 25 l over a 20 minute period, and the active ingredient was trapped in a silica gel trap and quantitatively analyzed.

The trap was set 100 cm away from the side wall and 150 cm high from the floor. The concentration of the active ingredient per $m^3$ of air was calculated from the amount of the collected active ingredient in accordance with the following formula:

$$\text{Airborne Concentration of Active Ingredient } (\mu g/m^3) = R \times [1000(l)/25.0(l) \times 20(\text{min})]$$

wherein R is the amount of the collected active ingredient ($\mu$g).

In the above test, empenthrin was used as an active ingredient.

The results obtained were compared with those of the test conducted in the same manner but using a conventional liquid type electric mosquito control apparatus.

Furthermore, a fan type insect pest control apparatus having fitted thereto a honeycomb carrier (66×66×15 mm) impregnated with 4.3 g of empenthrin and 0.2 g of Irganox 1010 was placed in a room having a capacity of 24 $m^3$, and the fan was driven at 1220 to 1250 rpm, at 25° C., and at a constant voltage of 3 V. Air of the room was sucked up and trapped by a silica gel trap in the same manner as described above (i.e., 25 l/min for 20 minutes to trap 500 l of air in total). An average airborne concentration of the active ingredient was obtained from the result of the air collected at a height of 150 cm and that at a height of 75 cm. The results of the liquid type electric mosquito control apparatus were used as a standard for comparison. The state of vaporization for 12 hours from the start of release is shown in the graph of FIG. 7, in which ○ indicates the airborne concentration of empenthrin (driven at a constant voltage of 3 V), and ⊙ indicates the airborne concentration of prallethrin (liquid type electrical mosquito control apparatus).

The release of empenthrin in long-term intermittent running of the fan type insect pest control apparatus (12 hours a day for consecutive 30 days) was also observed in the same experimentation system. The results obtained over the testing period of from the start of release up to 360 hours are plotted in the graph shown in FIG. 8. The graph also includes the comparative results obtained from the liquid type electric mosquito control apparatus put in the room shown in FIG. 6 at the same position as the fan type insect pest control apparatus and electrically heated to vaporize the liquid preparation. In the graph of FIG. 8, ○ indicates the vaporization amount of empenthrin (driven at a constant voltage of 3 V), and Δ indicates the vaporization amount of prallethrin (liquid type electric mosquito control apparatus).

It is seen from both Figures that the fan type insect pest control apparatus releases a larger amount of the active ingredient than the liquid type electric mosquito control apparatus and attains an equilibrium concentration within the first 30 minute period and thereafter keeps releasing uniformly and stably over 360 hours.

If the blowing operation in the fan type insect pest control apparatus of the present invention is controllable, the amount of the preparation to be released could thereby be controlled, which will not only ensure further improvement in uniformity and stability of vaporization but, under some situations, make it feasible to control an increase and a decrease of the amount vaporized with time (from daytime to nighttime). The fan type insect pest control apparatus was experimentally run while controlling blowing by using a circuit for controlling the quantity of electricity supplied from a power source as shown in FIG. 9. The above-described empenthrin preparation was released for a 12-hour testing period by continuous blowing or by controlled intermittent blowing (repetition of 2-hour blowing followed by 10-minute suspension). The results obtained are shown in FIG. 10. The results prove that the active ingredient airborne concentration can be maintained constant even though the blowing cycle is under control.

The control circuit of FIG. 9 is explained below.

The control circuit comprises DC power source 101 which converts the power from a commercial power source to a prescribed DC voltage; frequency distinguishing part 103 which distinguishes commercial power frequencies; frequency dividing part 106 which divides the commercial power frequency into 5 or 6 based on the distinction made by frequency distinguishing part 103 to obtain reference pulses of 10 Hz; pulse producing part 107 which sends pulses for a prescribed period of time based on the output of frequency dividing part 105; luminance modulating part 111 for lighting or blinking light-emitting diode (LED) 109 for externally displaying the operating state of the apparatus; thyristor 115 which feeds power to driving motor 113; zerocross control part 117 which controls thyristor 115 at zero voltage; and mode controller 119 which instructs luminance modulator 111 on blinking or lighting in accordance with an external operation and also conduct trigger control on zerocross control part 117 so as to fire a triac based on the previously set sequence.

By using the control circuit, an appropriate blowing control mode can be put in mode controller 119, and the triac is triggered via zerocross control part 117 thereby to control the operation of the blower.

On user's choice of sequence mode according to the necessity, the operation of the blower is controlled based on the chosen sequence mode, and vaporization of the preparation is controlled accordingly.

The circuit is also provided with a manual program setting function for allowing a user to set a sequence mode arbitrarily.

While the position of the preparation-retaining material in the air passageway may be either on the air intake side or the vapor outlet side of the blowing means, the latter position is preferred because the air current applied to the carrier is relatively uniform irrespective of the position of the carrier within the air passageway. In this case, the carrier is set in the air current sucked up from the air intake toward the fan.

The place in which the insect pest control apparatus is effective is not limited. Places partitioned off to have a given space are preferred. For example, the apparatus is suitably used in houses, greenhouses, septic tanks, and the like to control the insect pests living there. Insect pests on which the apparatus is effective include house insects, such as flies, mosquitos, cockroaches, house dust mites, and other disgusting insects invading from the outdoors; insects in wardrobes or chests which are harmful to clothes, such as tineid moths, webbing clothes moths, dermestid beetles and the like; insects in greenhouses which are harmful to crops planted therein; insects in livestock houses, such as biting midges, flies, mosquitos, mites and the like; and insects in septic tanks, such as moth flies, mosquitos and the like.

Effect:

As described above, it has been generally accepted that a pesticidal component which is hard to vaporize at normal temperature (about 15 to 35° C.) is not effective in controlling insect pests unless it is heated at about 110° to 170° C.

The inventors of the present invention studied the vapor pressure vs. temperature relationship for a great number of pesticidal components and have made it clear that the vapor pressure-temperature relationship of the components, put in order on a cox diagram, can be represented by straight lines parallel to each other. Based on this result of study, it has now been found that a preparation-retaining material in which an insect pest control agent having a vapor pressure lower than $1\times10^{-3}$ mmHg ($1\times10^{-3}$ to $1\times10^{-7}$ mmHg) at 30° C. on the cox diagram, sparing vaporizablity at normal temperature, and a boiling point of not lower than 120° C./1 mmHg is supported on an appropriate carrier is, when fixed and given an air current under non-heating conditions, capable of controlling not only flying insect pests but cockroaches and the like.

When the insect pest control apparatus of the present invention is used, there is no danger of fire because no heating is required. Furthermore, the pesticidal component can be released in a wide space in an effective concentration, and the effect lasts long. Therefore, insect pests can be controlled effectively.

The effect of the present invention will be demonstrated below by way of Examples.

EXPLANATION OF REFERENCE NUMBERS

Figure 1:
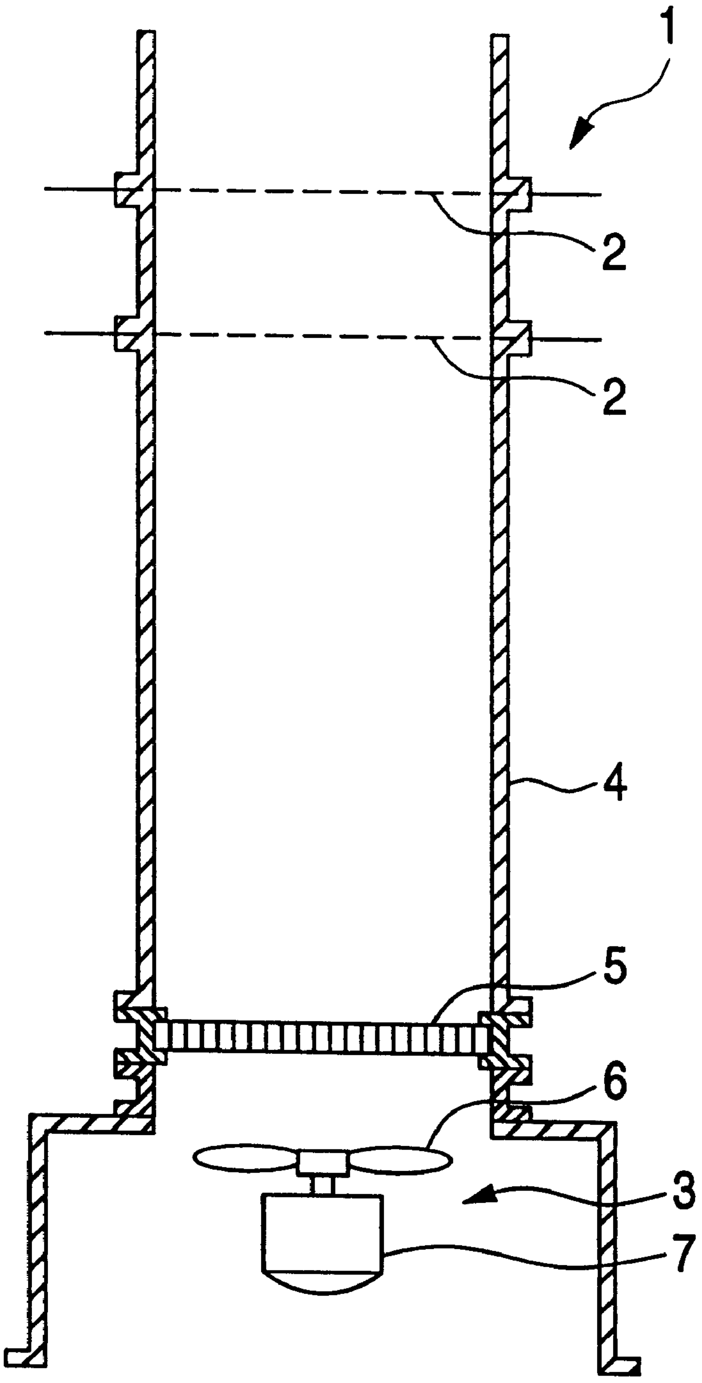
FIG. 1 is a schematic illustration showing one example of an apparatus for testing the pesticidal effect.

1 . . . Testing apparatus
2 . . . Insect net
3 . . . Blower
4 . . . Acrylic resin cylinder
5 . . . Preparation-retaining material
6 . . . Propeller fan
7 . . . Motor
12 . . . Air intake
13 . . . Air passageway
14 . . . Vapor outlet
15 . . . Battery
16 . . . Battery box
17 . . . Switch
20 . . . Ventilation means (propeller)
21 . . . Ventilation means (electric motor)
30 . . . Carrier (retaining material)
31 . . . Carrier cover
40 . . . Current regulator
41 . . . Plate
42 . . . Sirocco fan
43 . . . Motor
44 . . . Vapor outlet
50 . . . Testing room
51 . . . Fan type insect pest control apparatus
52 . . . Insect cage (1)
53 . . . Insect cage (2)
54 . . . Silica gel trap (1)
55 . . . Silica gel trap (2)
56 . . . Current meter (1)
57 . . . Vacuum pump (1)
58 . . . Current meter (2)
59 . . . Vacuum pump (2)
60 . . . Exhaust duct
81 . . . Constant temperature water bath
82 . . . Heater
83 . . . Stirrer
84 . . . Lead wire
85 . . . Condenser
86 . . . Manometer
87 . . . Constant pressure bottle
88 . . . Water jet pump
101 . . . DC power source
103 . . . Frequency distinguishing part
105 . . . Frequency dividing part
107 . . . Pulse producing part
109 . . . Light-emitting diode (LED)
111 . . . Luminance modulating part
113 . . . Driving motor
115 . . . Thyristor
117 . . . Zerocross control part
119 . . . Mode controller

BEST MODES FOR CARRYING OUT THE INVENTION

The present invention will be explained specifically with reference to Examples, but it should be understood that the present invention is not limited thereto.

EXAMPLE 1

Testing apparatus 1 shown in FIG. 1 comprising acrylic resin cylinder 4 was used. Twenty of northern house mosquitos (female adult) were put in the space partitioned with insect nets 2 and 2, and blower 3 was set at the bottom of testing apparatus 1. Preparation-retaining material 5 comprising a honeycomb carrier impregnated with a preparation was fitted in at the lower part of cylinder 4 and above blower 3. Air was blown from the bottom of cylinder 4 and passed through the preparation-retaining material 5 to release the pesticidal component from the preparation, and the insecticidal effect was examined using apparatus 1 for insect control of the present invention.

The number of knockdowns of the mosquitos was counted for every 30 seconds during 10 minutes and 30 seconds following the start of the testing. The mosquitos knocked down were transferred to a clean plastic cup (volume: about 500 ml) containing a cotton wad impregnated with a 1% aqueous sugar solution as feed, and the cup was covered and maintained under constant temperature conditions of about 25° C. The mortality after 24 hours was observed. The results obtained are shown in Table 2 below.

TABLE 2

Results of Insecticidal Test

| | Examples | | | | | Example |
|---|---|---|---|---|---|---|
| | teralle-thrin | prall-thrin | fura-methrin | es-biol | res-methrin | empen-thrin |
| Number of Insects * | 17 | 22 | 19 | 22 | 19 | 25 |
| Time (min): | | | | | | |
| 0.5 | 0 | 0 | 0 | 0 | 0 | 0 |
| 1.0 | 0 | 0 | 0 | 0 | 0 | 0 |
| 1.5 | 4 | 1 | 0 | 1 | 0 | 1 |
| 2.0 | 15 | 10 | 1 | 3 | 0 | 2 |
| 2.5 | 17 | 15 | 3 | 10 | 2 | 5 |
| 3.0 | | 21 | 8 | 17 | 2 | 10 |
| 3.5 | | 22 | 18 | 19 | 4 | 16 |
| 4.0 | | | 19 | 22 | 5 | 25 |
| 4.5 | | | | | 5 | |
| 5.0 | | | | | 7 | |
| 5.5 | | | | | 7 | |
| 6.0 | | | | | 8 | |
| 6.5 | | | | | 10 | |
| 7.0 | | | | | 12 | |
| 7.5 | | | | | 13 | |
| 8.0 | | | | | 16 | |
| 8.5 | | | | | 17 | |
| 9.0 | | | | | 19 | |
| 9.5 | | | | | | |
| 10.0 | | | | | | |
| 10.5 | | | | | | |

TABLE 2-continued

| Results of Insecticidal Test | | | | | | |
|---|---|---|---|---|---|---|
| | Examples | | | | | Example |
| | teralle-thrin | prall-thrin | fura-methrin | es-biol | res-methrin | empen-thrin |
| Mortality (%): | | | | | | |
| 24hrs. | 88 | 86 | 100 | 70 | 58 | 96 |
| 48hrs. | 100 | 100 | 100 | 78 | 79 | 100 |

Note:
Test Insect:
Northern house mosquito (female adult)
Test Conditions:
Temperature: 26 to 30° C.
Honeycomb carrier: 70 × 70 × 15 mm
Amount of the preparation: 560 mg The preparation-retaining material used herein was prepared as follows. A honeycomb structure (70×70×15 mm) comprising a laminate of corrugated boards (single-sided) made of bleached kraft paper having a basis weight of 80 g/$m^2$ (height of the corrugation: about 2 mm) was uniformly impregnated with 3 ml of an acetone solution containing about 500 mg of preparation. The impregnated carrier was set in the apparatus after acetone vaporized.

The pesticidal components tested were terallethrin, empenthrin, prallethrin, furamethrin, esbiol, and resmethrin.

The vapor pressure of the tested pesticidal components at 30° C. on the cox diagram are shown in Table 3 below.

TABLE 3

| Preparation | Vapor Pressure at 30° C. (mmHg) |
|---|---|
| empenthrin | $1.5 \times 10^{-3}$ |
| terallethrin | $6.6 \times 10^{-4}$ |
| prallethrin | $1.3 \times 10^{-4}$ |
| furamethrin | $4.5 \times 10^{-4}$ |
| esbiol | $1.2 \times 10^{-4}$ |
| resmethrin | $1.7 \times 10^{-5}$ |

Test Results:

As is apparent from Table 2, the tested pesticidal components, while having a vapor pressure as low as from $1\times10^{-3}$ mmHg to $1\times10^{-6}$ mmHg, achieve a lethal activity of 100 to 80% when applied to the method of the present invention comprising applying an air current to the preparation-retaining material, exhibiting an extremely excellent control effect on insect pests.

EXAMPLE 2

Figure 6:
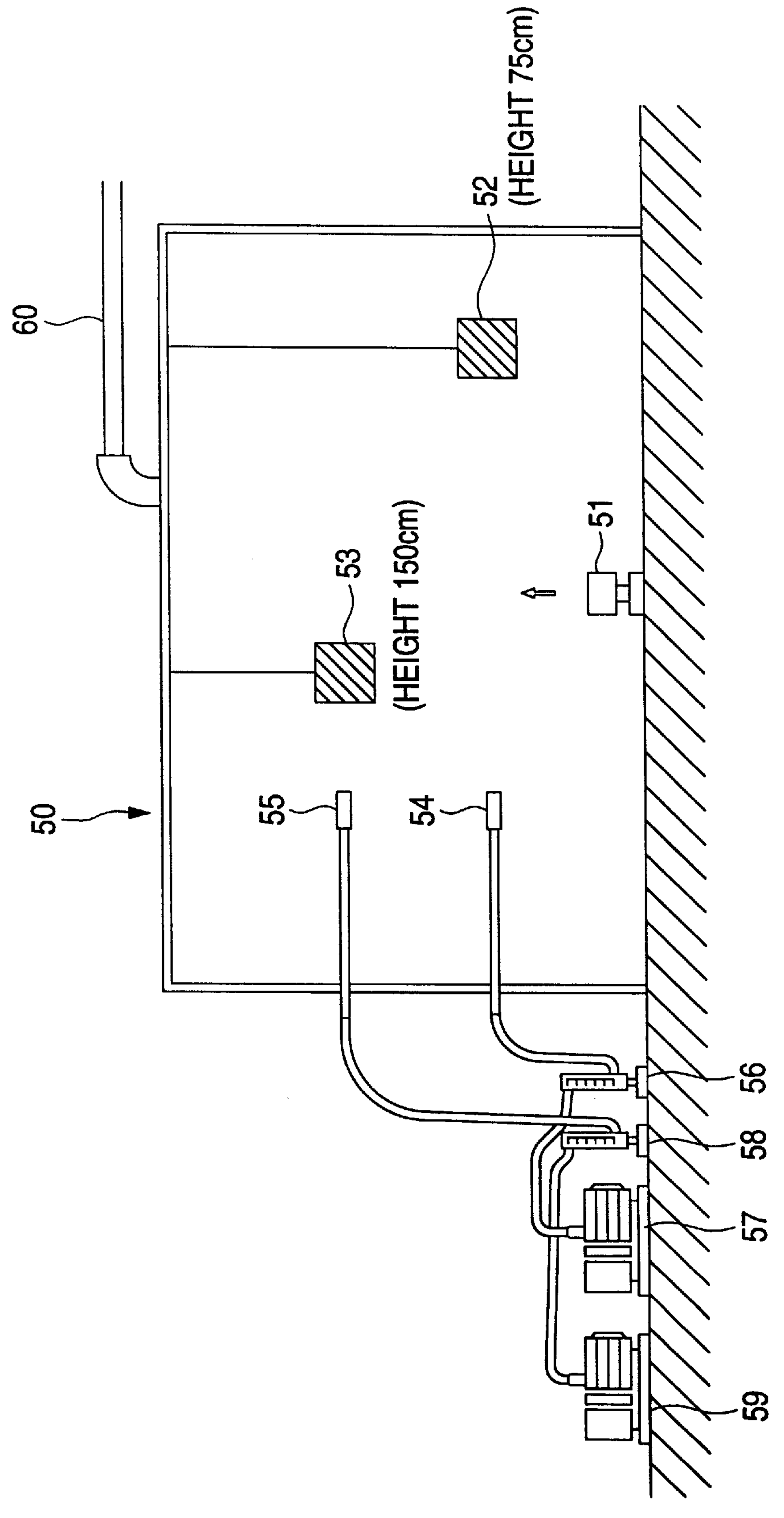
FIG. 6 schematically illustrates one example of a system for determining the airborne concentration of a pesticidal preparation vaporized.
Figure 7:
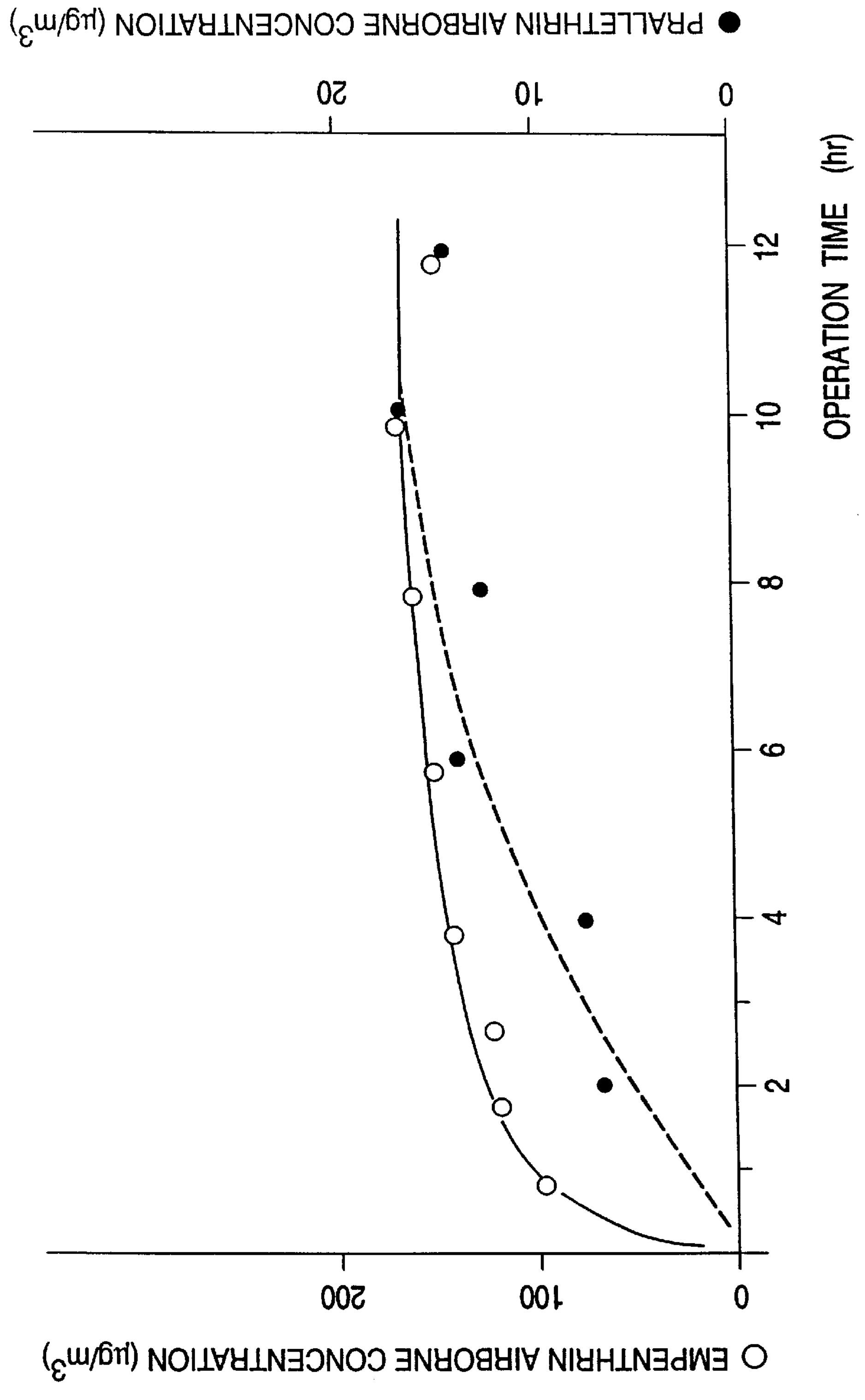
FIG. 7 is a graph of the airborne concentrations of the active ingredient released from a fan type insect pest control apparatus and a liquid type electric mosquito control apparatus.
Figure 8:
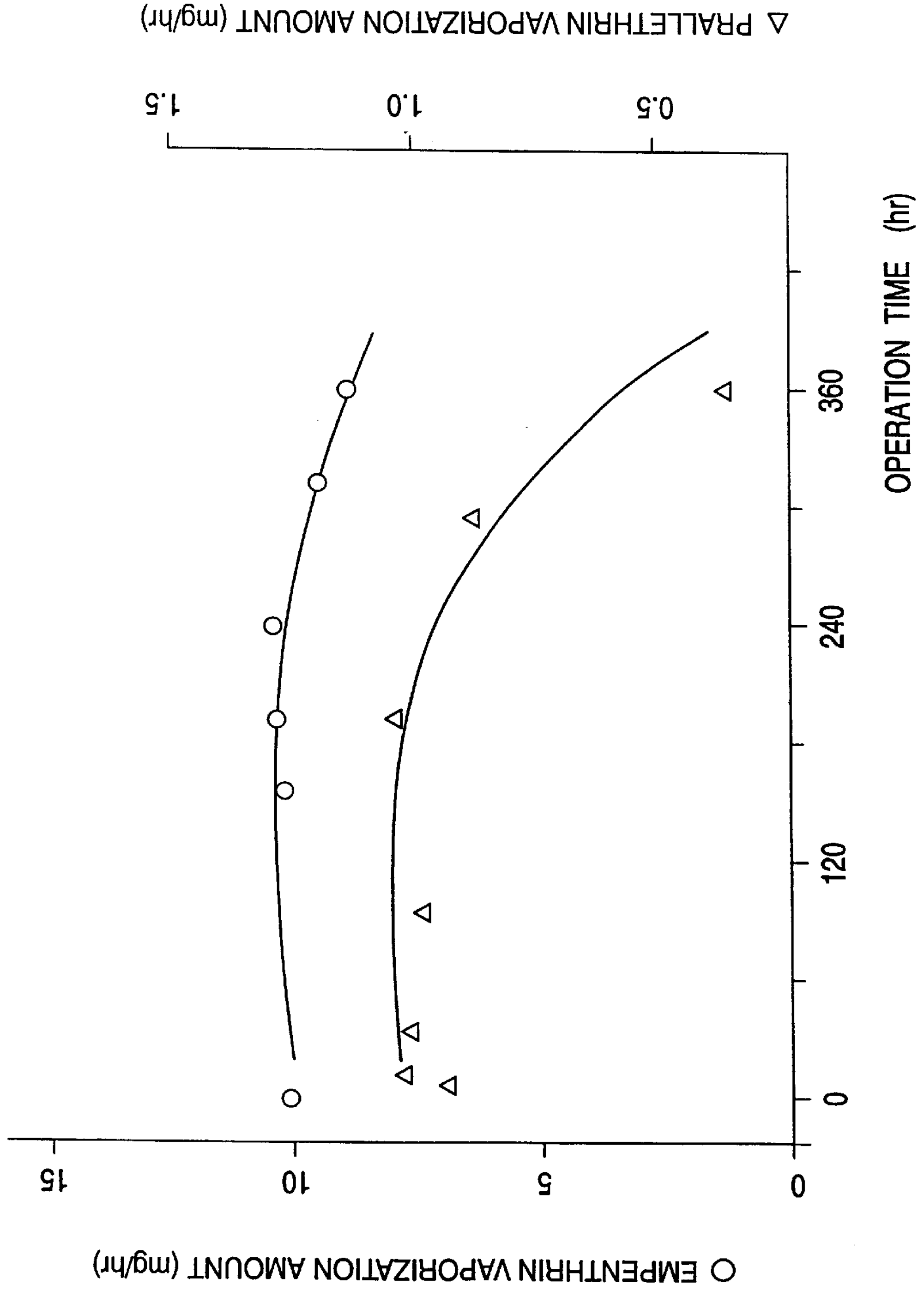
FIG. 8 is a graph showing the vaporizing behavior of the active ingredient from a fan type insect pest control apparatus and a liquid type electric mosquito control apparatus.
Figure 9:
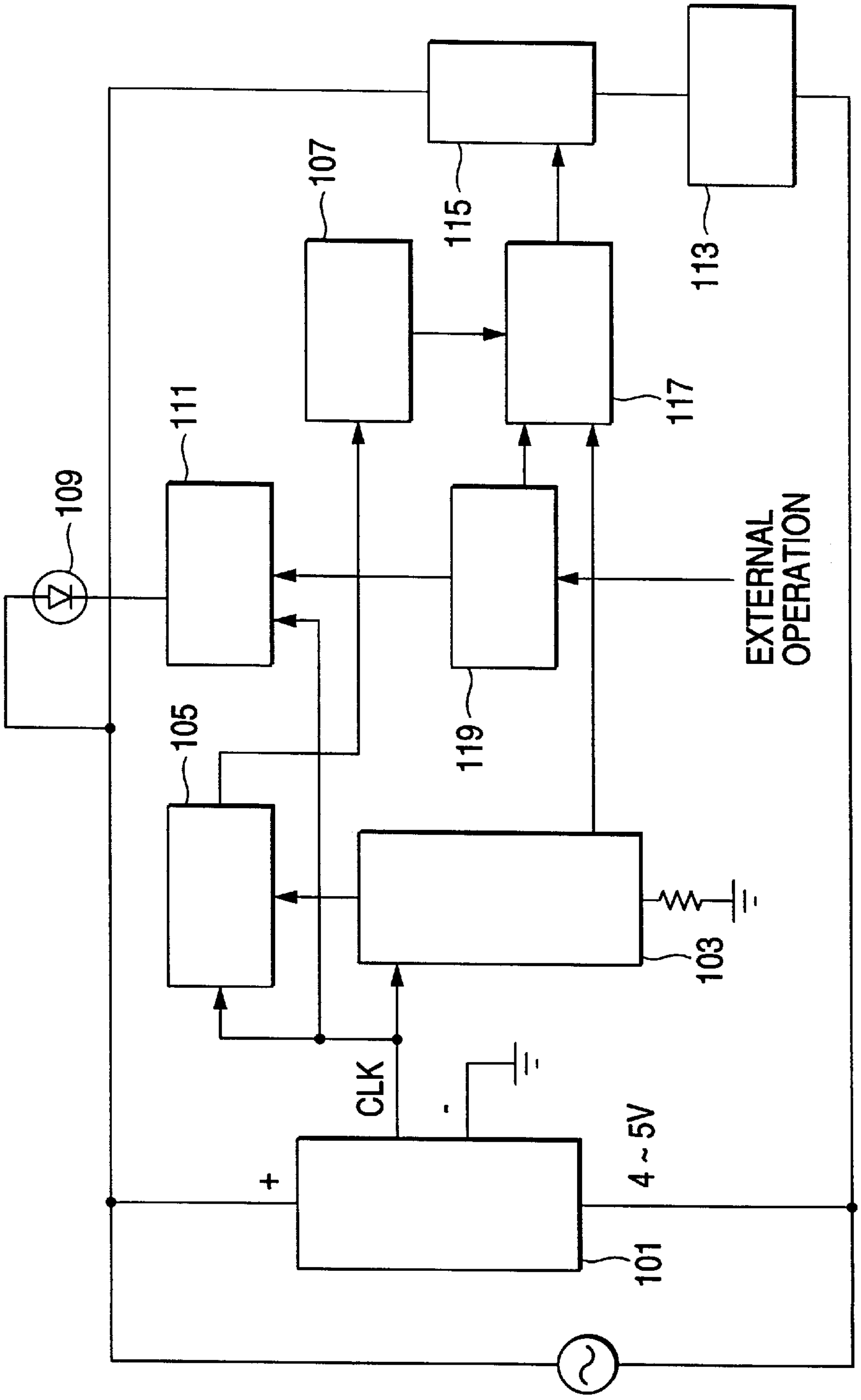
FIG. 9 is one example of a control circuit for controlling the operation of the blower in a fan type insect pest control apparatus.
Figure 10:
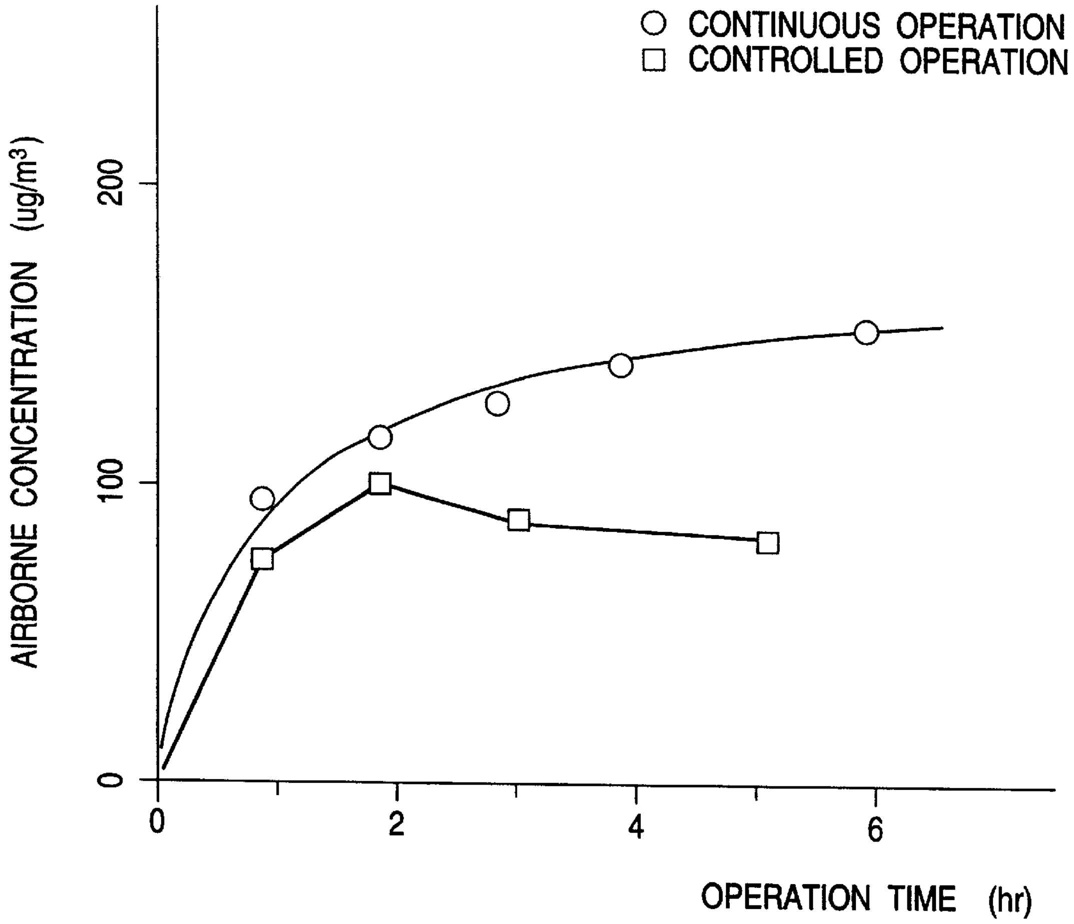
FIG. 10 is a graph showing the vaporization of empenthrin from a fan type insect pest control apparatus with the operation of the blower controlled.
Figure 11:
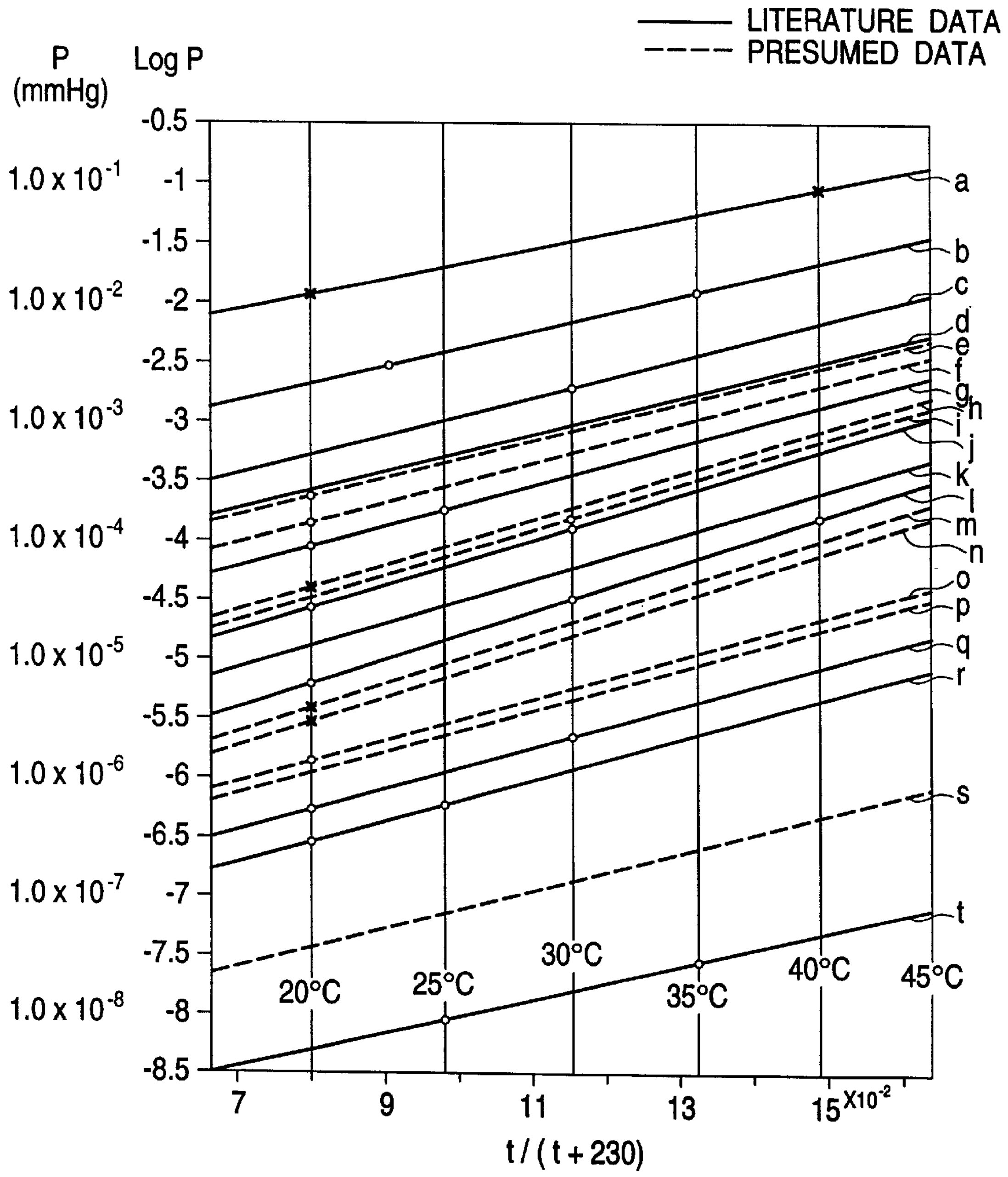
FIG. 11 is one example of a cox diagram representing the vapor pressure-temperature relationship of pesticidal components.
Figure 12:
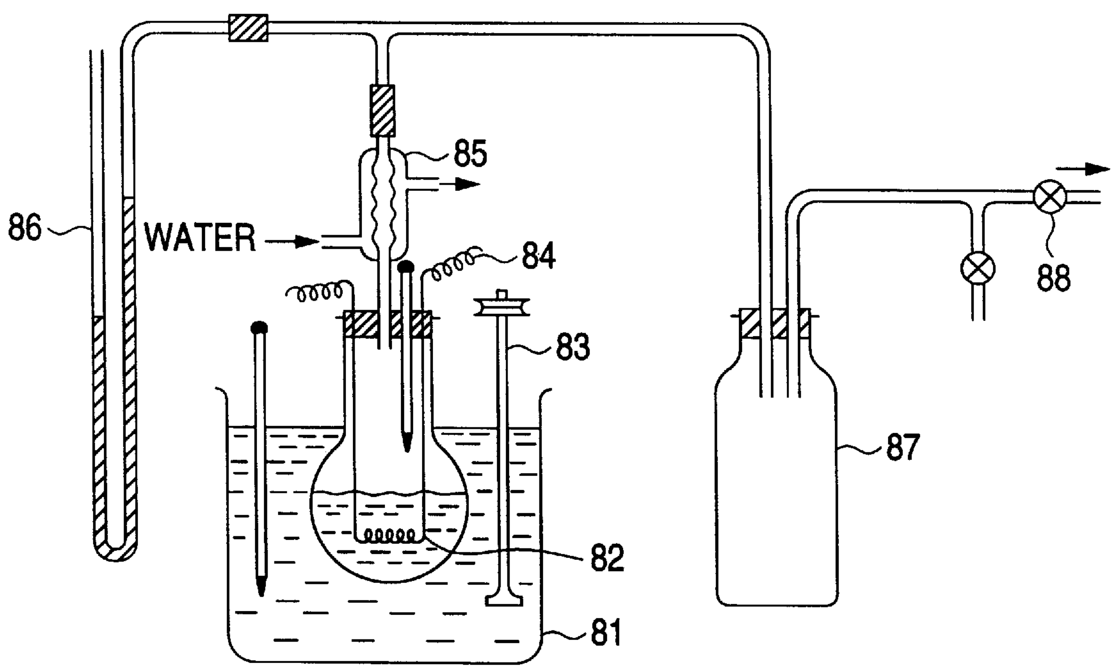
FIG. 12 illustrates a method of vapor pressure measurement.

A test on insecticidal effect on common mosquitos was carried out using the system for determining airborne concentrations shown in FIG. 6 (spatial capacity: 24 $m^3$).

Figure 2:
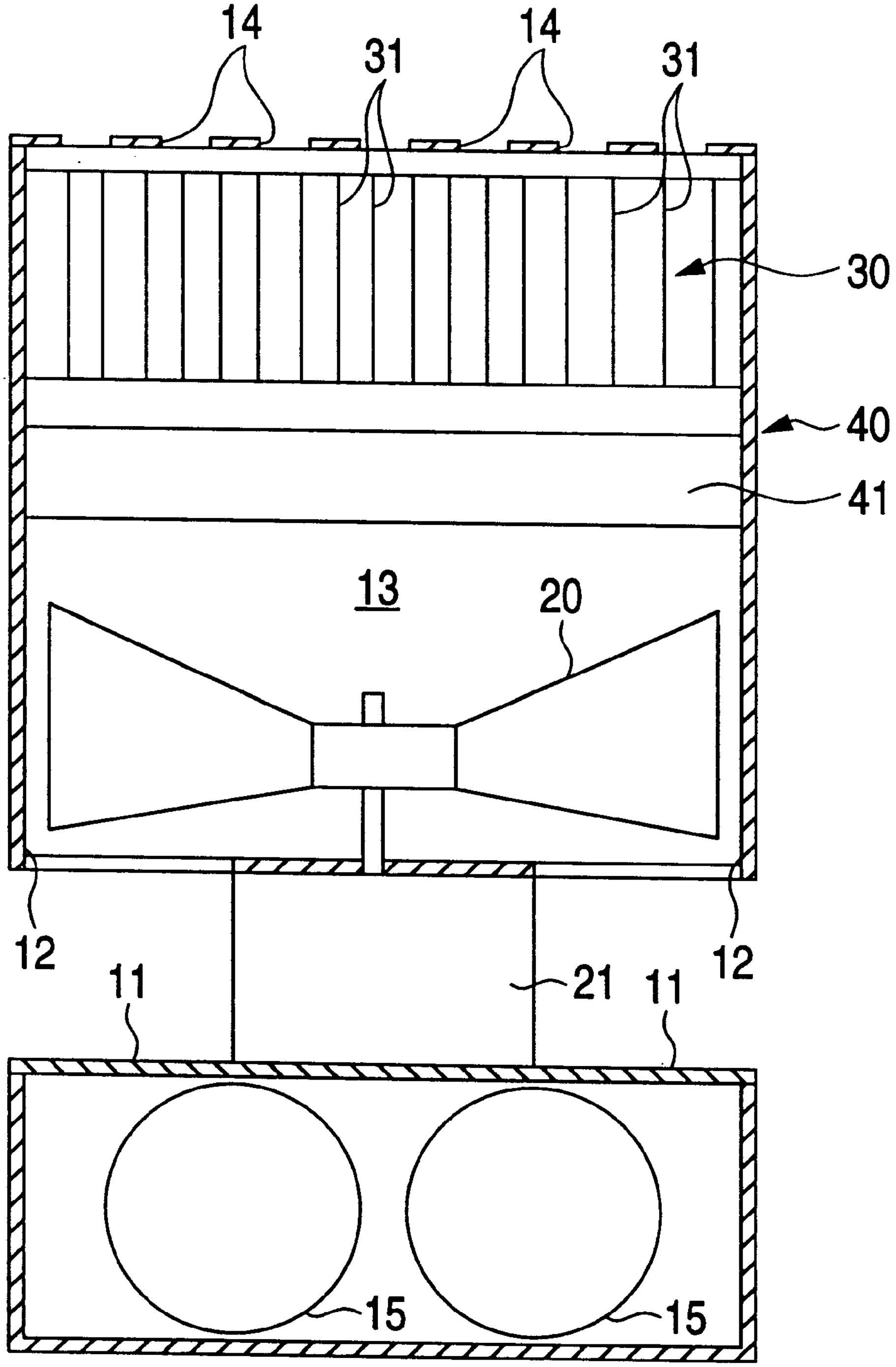
FIG. 2 is a schematic illustration showing one example of a fan type insect pest control apparatus in which a pesticidal preparation is used.

A fan type insect pest control apparatus having the structure shown in FIG. 2 and having fitted thereto a honeycomb carrier (70×70×15 mm) impregnated with 4.5 g of empenthrin was put at the prescribed position of the system. For comparison, a commercially available liquid type electric mosquito control apparatus using prallethrin was used.

Two cages each containing 20 to 25 of northern house mosquitos (female adult) were set 150 cm or 75 cm high from the floor. The apparatus was operated for 2 hours. A tester entered the room for every 10 minutes and counted the number of knockdowns. After the test, the insects knocked down were put in a plastic cup. Twenty-four hours later, the number of dead insects was counted. The results obtained are shown in Table 4 below. It is seen that the fan type apparatus and liquid type electric apparatus (prallethrin) are equal in knockdown effect in terms of $KT_{50}$ and that the former is superior to the latter in lethal effect.

TABLE 4

| | $KT_{50}$ (min) Height from Floor | | | Mortality after 24 Hours (%) Height from Floor | | |
|---|---|---|---|---|---|---|
| | 150 cm | 75 cm | Average | 150 cm | 75 cm | Average |
| Fan type | 69 | 69 | 64 | 51 | 59 | 55 |
| Liquid type | 102 | 82 | 92 | 11 | 15 | 13 |

EXAMPLE 3

A test was carried out in a test room having a spatial volume of 24 $m^3$ under the following conditions, and the knockdown ratio (after 24 hours) and the mortality (%) in cockroaches were examined.

The insect pest control apparatus of the present invention was put at the center of the floor of the room, and two cups each containing 20 cockroaches were placed at each of the two opposite corners of the floor. The pesticidal component shown in Table 5 below was released from the apparatus for consecutive 24 hours. As test insects, sensitive German cockroaches (*Blatella germanica*) and sensitive smoky-brown cockroaches (*Periplaneta fuliginosa*) were used.

Figure 3:
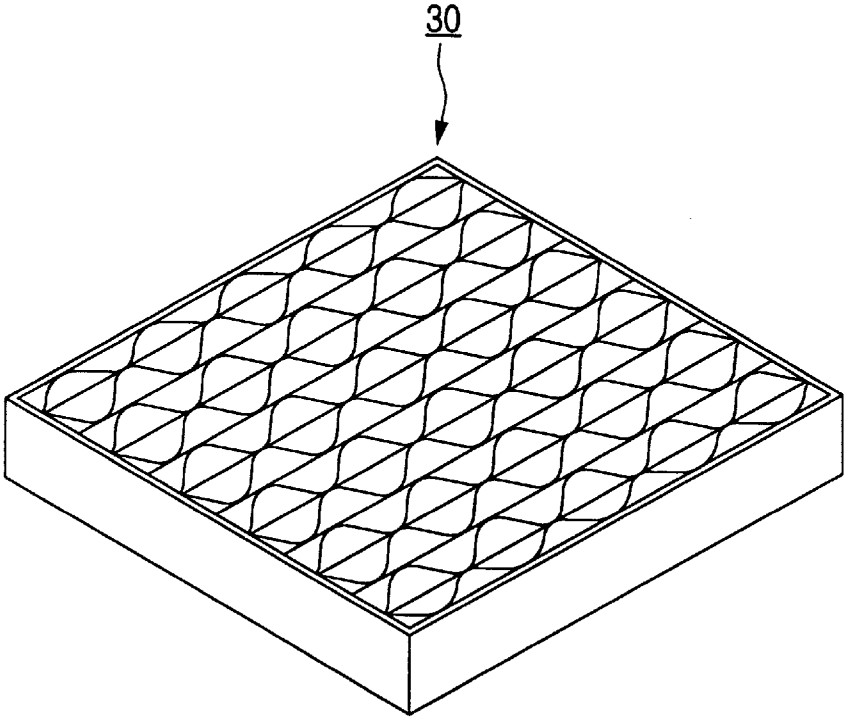
FIG. 3 is a perspective view of one example of a carrier for a pesticidal preparation.
Figure 4:
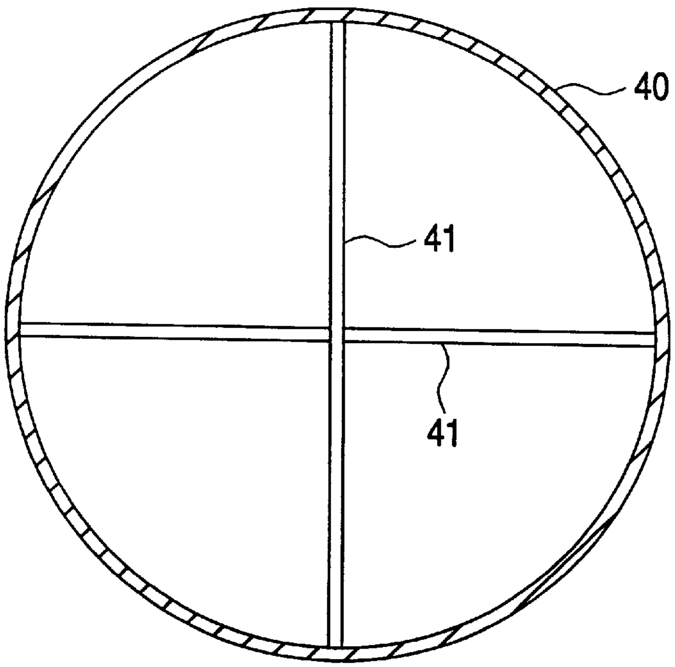
FIG. 4 is a side view of one example of a current regulator to be used in a fan type pesticidal apparatus.
Figure 5:
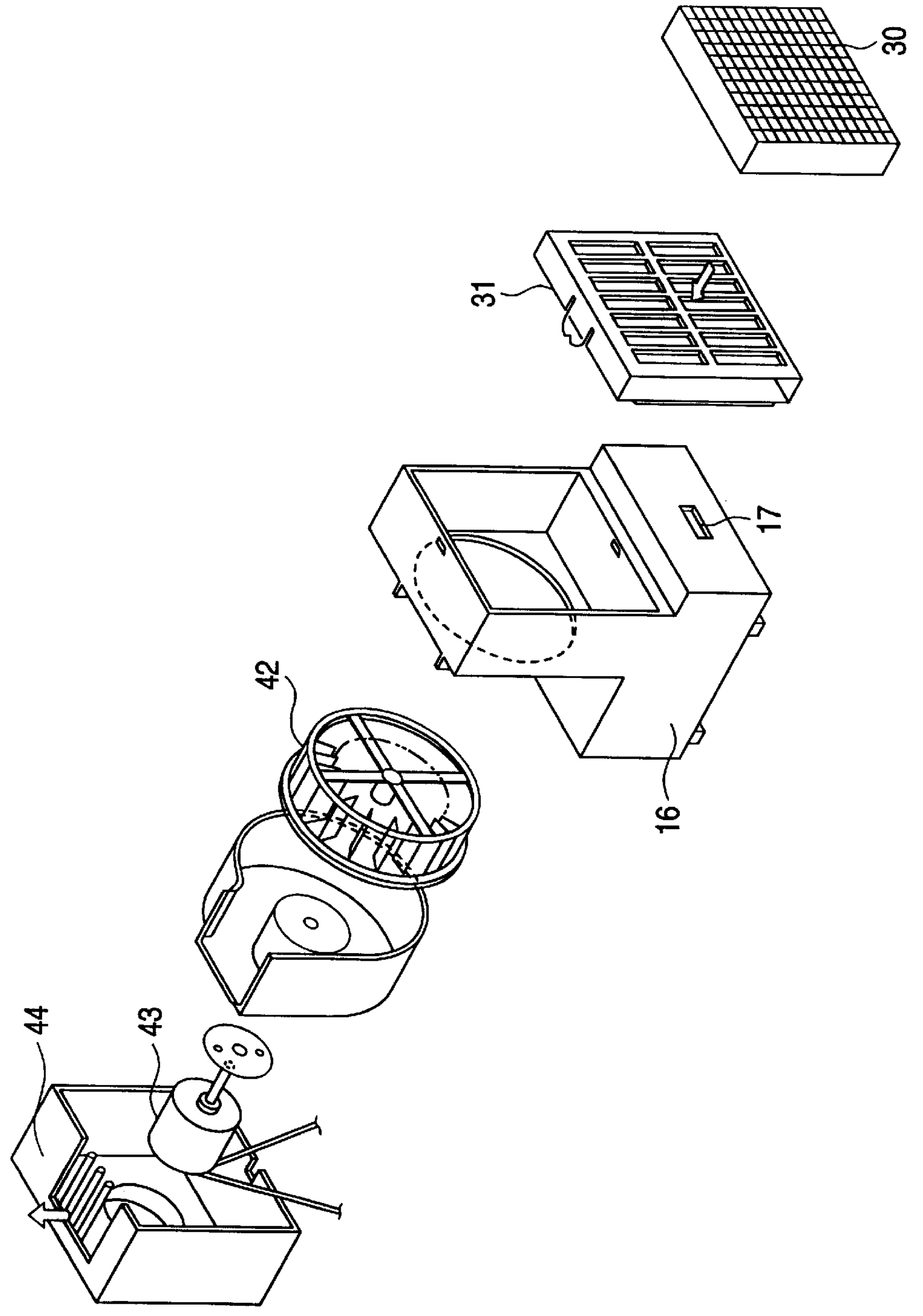
FIG. 5 illustrates one example of a fan type pesticidal apparatus equipped with a sirocco fan.

The preparation-retaining material used was prepared by impregnating a honeycomb carrier (70×70×15 mm; FIG. 3) with 1.0 g of the pesticidal component.

The results obtained are shown in Table 5.

TABLE 5

| | Pesticidal Component | | | |
|---|---|---|---|---|
| | Benfluthrin | | Empenthrin | |
| Knockdown Ratio (%) | German Cockroach (Sensi-tivity) | Smokybrown Cockroach (Sensi-tivity) | German Cockroach (Sensi-tivity) | Smokybrown Cockroach (Sensi-tivity) |
| 1 hr | 0 | 0 | 0 | 0 |
| 2 hrs | 0 | 0 | 0 | 0 |
| 4 hrs | 0 | 5.0 | 0 | 0 |
| 24 hrs | 87.5 | 6.3 | 90.0 | 65.0 |
| Mortality at 48 hrs (%) | 97.5 | 7.5 | 90.0 | 75.0 |

EXAMPLE 4

| Formulations for Honeycomb Impregnation: | |
|---|---|
| No. 1: | |
| empenthrin | 4.0 g |
| N-benzoylvaline | 0.05 g |

-continued

| Formulations for Honeycomb Impregnation: | |
|---|---|
| ethanol | 0.50 g |
| Irganox 1010 (Ciba-Geigy Corporation) (tetrakis [methylene-3-(3,5-di-t-butyl-4-hydroxyphenyl)propionate) | 0.1 g |
| The above composition was infiltrated into a honeycomb carrier of 66 × 66 × 15 mm. | |
| No. 2 | |
| empenthrin | 1.0 g |
| 2,2'-methylenebis(4-methyl-6-t-butylphenol) | 0.15 g |
| piperonyl butoxide | 1.5 g |
| The above composition was infiltrated in a honeycomb carrier of 50 × 50 × 15 mm. | |
| No. 3: | |
| benfluthrin | 0.5 g |
| bisphenol A | 0.02 g |
| isostearyl palmitate | 0.05 g |
| The above composition was infiltrated in a honeycomb carrier of 35 × 35 × 10 mm. | |
| No. 4: | |
| benfluthrin | 2.0 g |
| N-hexanoyl-ε-aminocaproic acid | 0.03 g |
| isopropyl myristate | 0.15 g |
| The above composition was infiltrated in a honeycomb carrier of 70 × 35 × 15 mm. | |
| No. 5: | |
| allethrin | 1.5 g |
| S-421 | 1.5 g |
| 2,6-di-t-butylhydroxytoluene | 0.2 g |
| The above composition was infiltrated in a honeycomb carrier of 50 × 50 × 20 mm. | |
| No. 6: | |
| tetramethrin | 1.3 g |
| 4,4'-butylidene-bis(3-methyl-6-t-butylphenol) | 0.01 g |
| The above composition was infiltrated in a honeycomb carrier of 50 × 50 × 10 mm. | |
| No. 7: | |
| prallethrin | 0.5 g |
| 2-hydroxy-4-n-octylbenzophenone | 0.2 g |
| The above composition was infiltrated in a honeycomb carrier of 30 × 30 × 20 mm. | |

EXAMPLE 5

| Formulations for Solutions: | |
|---|---|
| No. 8: | |
| empenthrin | 5.0 g |
| 2,6-di-t-butylhydroxytoluene | 0.6 g |
| perfume | 0.1 g |
| kerosine | 35 ml |
| No. 9: | |
| benfluthrin | 0.6 g |
| 2,6-di-t-butylhydroxytoluene | 0.1 g |
| perfume | 0.1 g |
| isoopropyl myristate | 8 ml |
| kerosine | 32 ml |
| No. 10: | |
| prallethrin | 1.3 g |
| 2,6-di-t-butylhydroxytoluene | 0.1 g |

-continued

| Formulations for Solutions: | |
|---|---|
| perfume | 0.1 g |
| kerosine | 40 ml |

EXAMPLE 6

| Water-based Formulations: | |
|---|---|
| No. 11: | |
| benfluthrin | 0.6 g |
| butyl carbitol | 25 ml |
| water | 25 ml |
| butylhydroxytoluene | 0.20 g |
| No. 12: | |
| empenthrin | 2.0 g |
| butyl carbitol | 25 ml |
| propylene glycol | 17 ml |
| water | 8 ml |
| butylhydroxytoluene | 0.20 g |

INDUSTRIAL APPLICABILITY

Currently available insect pest control methods and apparatus using effective pesticidal components are of the type that the active ingredient of a pesticidal preparation is vaporized and diffused under heating conditions. However, the methods and apparatus used under heating conditions are accompanied by an increase in temperature of the equipment or surrounding temperature, involving a danger of a burn.

On the other hand, known insect pest control means using preparations which are effective under non-heating conditions, such as DDVP, involves a safety problem.

Preparations which are known to be effective in insect pest control but are not considered to be released in a concentration sufficient for insect pest control under non-heating conditions only by blowing have been studied systematically by analyzing the vapor pressure vs. temperature relationship plotted on a cox diagram. As a result, it has been found that an extremely excellent pesticidal effect can be obtained simply by blowing air under non-heating conditions by using a safe and yet effective pesticidal component which is hard to vaporize at normal temperature, preferably a component having a vapor pressure of higher than $1\times10^{-7}$ mmHg at 30° C., still preferably a component having a vapor pressure of higher than $1\times10^{-7}$ mmHg and a boiling point of not lower than 120° C./1 mmHg.

Therefore, the present invention makes it feasible to develop a method and an apparatus for controlling insect pests which are simpler and safer than the conventional ones.

What is claimed is:

1. An insect pest control method which comprises: positioning in an insect pest control apparatus a preparation-retaining material which comprises a preparation containing at least one pesticidal component selected from at least one compound which has a vapor pressure of $1\times10^{-7}$ mmHg to $1\times10^{-3}$ mmHg at 30° C. supported on a carrier having a ventilation structure so that an air current raised by a blower means is passed into and through the carrier thereby releasing the pesticidal component from the preparation-retaining material into the air under non-heating conditions in an effective amount capable of knocking down and/or killing Smokeybrown cockroaches at a rate of at least 65% in a room of 24 $m^3$ within 24 hours or female adult northern house mosquitoes at a rate of at least 55% in a room of 24 $m^3$ within 24 hours, wherein said compound which has a vapor pressure of $1\times10^{-7}$ mmHg to $1\times10^{-3}$ mmHg at 30° C. is selected from the group consisting of d-trans-2,3,5,6-tetrafluorobenzyl-3-(2,2-dichlorovinyl)-2,2-dimethyl-1-cyclopropanecarboxylate, (5-benzyl-3-furyl)methyl d-cis/trans-chrysanthemate, d-3-allyl-2-methyl-4-oxo-2-cyclopentenyl d-trans-chrysanthemate, 5-propargyl-2-furylmethyl d-cis/trans-chrysanthemate, (+)-2-methyl-4-oxo-3-(2-propynyl)-2-cyclopentenyl (+)-cis/trans-chrysanthemate, dl-3-allyl-2-methyl-4-oxo-2-cyclopentenyl dl-cis/trans-2,2,3,3-tetramethylcyclopropanecarboxylate, isomers thereof, and structural analogues thereof;

wherein said air current is raised by a blowing means located in an air passageway in said insect pest control apparatus; and wherein said carrier is made of a material selected from the group consisting of paper, resin, ceramic, glass fiber, carbon fiber, chemical fiber, natural fiber, nonwoven fabric, porous glass material and metallic nets, and has a structure selected from the group consisting of a honeycomb structure, a ventilation blind, a lattice structure and a network structure.

2. The insect pest control method as claimed in claim 1, wherein said carrier has an air permeability of not less than 0.1 liter/sec.

3. The insect pest control method as claimed in claim 1, wherein said blowing means is a fan.

4. The insect pest control method as claimed in claim 3, wherein said fan has a revolution number of about 500 to 10,000 rpm.

5. An insect pest control apparatus which comprises:

a main body having a ventilation means connected to a vent hole; and a preparation-retaining material comprising a preparation supported on a carrier set at one or more locations within the ventilation means so as to be brought into contact with an air current raised at the vent hole under non-heating conditions, wherein said carrier is made of a material selected from the group consisting of paper, resins, ceramics, glass fiber, carbon fiber, chemical fiber, natural fiber, non-woven fabric, porous glass material and metallic nets and has a structure selected from the group consisting of a honeycomb structure, a ventilation blind, a lattice structure and a network structure, and the preparation-retaining material does not block an air current raised in the ventilation means and contains at least one pesticidal component selected from at least one compound which has a vapor pressure of $1\times10^{-7}$ mmHg to $1\times10^{-3}$ mmHg at 30° C. and is selected from the group consisting of d-trans-2,3,5,6-tetrafluorobenzyl-3-(2,2-dichlorovinyl)-2,2-dimethyl-1-cyclopropanecarboxylate, (5-benzyl-3-furyl)methyl d-cis/trans-chrysanthemate, d-3-allyl-2-methyl-4-oxo-2-cyclopentenyl d-trans-chrysanthemate, 5-propargyl-2-furylmethyl d-cis/trans-chrysanthemate, (+)-2-methyl-4-oxo-3-(2-propynyl)-2-cyclopentenyl(+)-cis/trans-chrysanthemate, dl-3-allyl-2-methyl-4-oxo-2-cyclopentenyl dl-cis/trans-2,2,3,3-tetramethylcyclopropanecarboxylate, isomers thereof, and structural analogues thereof, and wherein when an air current raised by a blower means is passed into and through the carrier the pesticidal component is released from the preparation-retaining material into the air under non-heating conditions in an effective amount capable of knocking down and/or killing Smokeybrown cockroaches at a rate of at least 65% in a room of 24 $m^3$ within 24 hours or female adult northern house mosquitoes at a rate of at least 55% in a room of 24 $m^3$ within 24 hours.

* * * * *